United States Patent [19]

Loose et al.

[11] Patent Number: 5,122,534

[45] Date of Patent: Jun. 16, 1992

[54] USE OF TENIDAP TO REDUCE TOTAL SERUM CHOLESTEROL, LDL CHOLESTEROL AND TRIGLYCERIDES

[75] Inventors: Leland D. Loose, Norwich; Naitee Ting, Ledyard, both of Conn.

[73] Assignee: Pfizer Inc., New York, N.Y.

[21] Appl. No.: 727,786

[22] Filed: Jul. 10, 1991

Related U.S. Application Data

[63] Continuation-in-part of Ser. No. 652,709, Feb. 8, 1991, abandoned.

[51] Int. Cl.$^5$ .............................................. A61K 31/40
[52] U.S. Cl. .................................... 514/414; 514/824
[58] Field of Search ................................ 514/414, 824

[56] References Cited

U.S. PATENT DOCUMENTS

| | | | |
|---|---|---|---|
| 4,556,672 | 12/1985 | Kadin | 514/414 |
| 4,853,409 | 8/1989 | Showell | 514/418 |
| 4,861,794 | 8/1989 | Otterness | 514/414 |
| 5,006,547 | 4/1991 | Loose | 514/414 |
| 5,008,283 | 4/1991 | Blackburn, Jr. et al. | 514/414 |

FOREIGN PATENT DOCUMENTS 277738 8/1988 European Pat. Off.

OTHER PUBLICATIONS

Ross et al., New England Journal of Medicine, 295:369-377 (1976).
Wallace, D. J. et al., Am. J. Medicine, 89:322-326 (1990).
Ku, G. et al., FASEB Journal, 4:1645-1653 (1990).
Svenson, K. L. G. et al., Arch. Intern. Med., 147:1917-1920 (1987).
Jelic-Ivanovic, Z. et al., Clinical Chemistry, 31:1141-1143 (1985).
Lakatos, J. et al., Clinical Biochemistry, 21:93-96 (1988).

*Primary Examiner*—Frederick E. Waddell
*Assistant Examiner*—Kimberly R. Jordan
*Attorney, Agent, or Firm*—Peter C. Richardson; J. Trevor Lumb; Gregg C. Benson

[57] ABSTRACT

This invention relates to the use of tenidap, presently shown as the enolic form of 5-chloro-2,3-dihydro-2-oxo-3-(2-thienylcarbonyl)-indole-1-carboxamide, and the pharmaceutically-acceptable base salts thereof to reduce total serum cholesterol, LDL cholesterol and triglycerides in a mammal having an inflammatory arthritic condition. The methods of this invention comprise administering an effective amount of tenidap or salts thereof to a mammal.

21 Claims, No Drawings

USE OF TENIDAP TO REDUCE TOTAL SERUM CHOLESTEROL, LDL CHOLESTEROL AND TRIGLYCERIDES

CROSS REFERENCE TO RELATED APPLICATION

This application is a continuation-in-part of copending application Ser. No. 07/652,709, filed Feb. 8, 1991, now abandoned.

TECHNICAL FIELD

This invention relates to the use of tenidap and the pharmaceutically-acceptable base salts thereof to reduce total serum cholesterol, LDL cholesterol and triglycerides in a mammal. The methods of this invention comprise administering an effective amount of tenidap or salts thereof to such a mammal.

BACKGROUND ART

Tenidap, presently shown as the enolic form of 5-chloro-2,3-dihydro-2-oxo-3-(2-thienylcarbonyl)-indole-1-carboxamide, has the structural formula

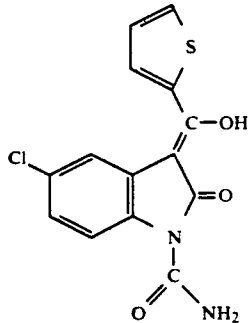

Tenidap and the pharmaceutically-acceptable base salts thereof, among other 3-substituted-2-oxindole-1-carboxamides, are disclosed and claimed in U.S. 4,556,672 which is assigned to the assignee hereof. That patent discloses that those compounds, in addition to being useful as anti-inflammatory and analgesic agents, are inhibitors of both the cyclooxygenase (CO) and lipoxygenase (LO) enzymes. The teachings thereof are incorporated herein by reference.

The use of tenidap and its pharmaceutically-acceptable base salts, among certain other 3-substituted-2-oxindole-1-carboxamides, to inhibit interleukin-1 biosynthesis in a mammal and to treat interleukin-1 mediated disorders and dysfunctions is disclosed in U.S. 4,861,794 which is assigned to the assignee hereof.

U.S. 4,853,409, assigned to the assignee hereof, discloses the use of tenidap and its pharmaceutically-acceptable base salts, among certain other 3-substituted-2-oxindole-1-carboxamides, to suppress T-cell function in a mammal and to treat T-cell mediated autoimmune disorders of the systemic or organ specific type.

An anhydrous, crystalline form of the sodium salt of tenidap is disclosed in European Patent Application 277,738 which has been filed in the name of the assignee hereof.

U.S. 5,008,283, assigned to the assignee hereof, discloses the use of tenidap and its pharmaceutically-acceptable base salts to inhibit activation of collagenase, treat collagenase mediated disorders and diseases and inhibit the activity of myeloperoxidase in a mammal.

U.S. 5,006,547, assigned to the assignee hereof, discloses the use of tenidap and its pharmaceutically-acceptable base salts to inhibit the release of elastase by neutrophils in a mammal and to treat elastase-mediated diseases and dysfunctions in a mammal.

Atherosclerosis, a disease of the arteries, is recognized to be the leading cause of death in the U.S. and Western Europe. The pathological sequence leading to atherosclerosis and occlusive heart disease has been described in detail by Ross and Glomset in New England Journal of Medicine 295, 369–377 (1976). The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Cholesterol and cholesteryl ester account for most of this lipid. Further, it is postulated that most of the cholesterol found within the fatty streaks results from uptake from the plasma. These fatty streaks, in turn, give rise to development of the "fibrous plaque", which consists of accumulated intimal smooth muscle cells laden with lipid and surrounded by extra cellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the arterial occlusion and tendency toward mural thrombosis and arterial muscular spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma triglyceride levels, cholesterol levels, and low density lipoprotein cholesterol levels in particular, as essential steps in prevention of CVD. The upper limits of "normal" are now known to be significantly lower than heretofore appreciated. As a result, large segments of Western populations are now realized to be at high risk for development or progression of CVD because of this factor. Individuals who possess independent risk factors in addition to hyperlipidemia are at particularly high risk. Such independent risk factors include glucose intolerance, left ventricular hypertrophy, hypertension, and being of the male sex. Successful treatment of hyperlipidemia in the general population is therefore of exceptional medical importance.

The first step in recommended therapeutic regimens for hyperlipidemia is dietary intervention. While diet alone produces adequate response in some individuals, many others remain at high risk and must be treated further by pharmacological means. New drugs for the treatment of hyperlipidemia are, therefore, of great potential benefit for large numbers of individuals at high risk of developing CVD.

Until the invention herein, there was no report of use or intent to use tenidap or the salts thereof to reduce total serum cholesterol levels, to reduce serum LDL cholesterol levels or to reduce serum triglycerides in a mammal.

DISCLOSURE OF INVENTION

It has been found that tenidap and the pharmaceutically-acceptable base salts thereof reduce the level of total serum cholesterol in a mammal having an inflammatory arthritic condition such as rheumatoid arthritis or osteoarthritis. Further, it has been found that tenidap and the pharmaceutically-acceptable base salts thereof reduce the level of serum LDL cholesterol in a mammal having an inflammatory arthritic condition such as rheumatoid arthritis or osteoarthritis. Further still, it has been found that tenidap and the pharmaceutically-acceptable base salts thereof reduce the level of serum triglycerides in a mammal having an inflammatory arthritic condition such as rheumatoid arthritis or osteoarthritis.

The method of using tenidap and its pharmaceutically-acceptable base salts comprises administering to a mammal an effective amount thereof. Administration can comprise any known method for therapeutically providing a compound to a mammal such as by oral or parenteral administration as defined hereinbelow.

DETAILED DESCRIPTION

Tenidap, its pharmaceutically-acceptable base salts and the preparation thereof are described in U.S. 4,556,672, the teaching of which are incorporated herein by reference. This invention concerns new uses for tenidap and its salts which comprise reducing the level of total serum cholesterol in a mammal having an inflammatory arthritic condition, reducing the level of serum LDL cholesterol in a mammal having an inflammatory arthritic condition and reducing the level of serum triglycerides in a mammal having an inflammatory arthritic condition. The term inflammatory arthritic condition is well known to those skilled in the art and includes, but is not limited to osteoarthritis and rheumatoid arthritis. Within the scope of this invention are methods for reducing the level of total serum cholesterol in a mammal in need thereof and having an inflammatory arthritic condition, methods for reducing the level of serum LDL cholesterol in a mammal in need thereof and having an inflammatory arthritic condition and methods for reducing the level of serum triglycerides in a mammal in need thereof and having an inflammatory arthritic condition.

As disclosed in U.S. 4,556,672, tenidap is acidic and forms base salts. All such base salts are within the scope of this invention and can be formed as taught by that patent. Such suitable salts, within the scope of this invention, include both the organic and inorganic types and include, gut are not limited to, the salts formed with ammonia, organic amines, alkali metal hydroxides, alkali metal carbonates, alkali metal bicarbonates, alkali metal hydrides, alkali metal alkoxides, alkaline eartgh metal hydroxides, alkaline earth metal carbonates, alkaline earth metal hydrides and alkaline earth metal alkoxides. Representative examples of bases which form such base salts include ammonia, primary amines, such as n-propylamine, n-butylamine, aniline, cyclohexylamine, benzylamine, p-toluidine, ethanolamine and glucamine; secondary amines, such as diethylamine, diethanolamine, N-methylglucamines, N-methylaniline, morpholine, pyrrolidien and piperidine; tertiary amines, such as triethylamine, triethanolamine, N,N-dimethylaniline, N-etylpiperidien and N-methylmorpholine; hydroxides, such as sodium hydroxide; alkoxides such as sodium ethoxide and potassium methoxide; hydrides such as calcium hydride and sodium hydride; and carbonates such as potassium carbonate and sodium carbonate. Preferred salts are those of sodium, potassium, ammonium, ethanolamine, diethanolamine and triethanolamine. Particularly preferred are the sodium salts. An anhydrous crystalline form of such a sodium salt is disclosed in European Patent Application 277,738, filed in the name of he assignee hereof. The teachings thereof which are incorporated herein by reference.

Also within the scope of this invention are the solvates such as the semihydrates and monohydrates of the compounds thereinavove described.

The methods of this invention comprise administering tenidap and the pharmaceutically-acceptable base salts thereof to a mammal. Such compounds and their salts can be administered to said mammal either alone or, preferably, in combination with pharmaceutically-acceptable carriers or diluents in a pharmaceutical composition, according to standard pharmaceutical practice. Such administration can be oral or parenteral. Parenteral administration as used herein includes, but is not limited to, intravenous, intramuscular, intraperitoneal, subcutaneous, transdermal and topical (including, but not limited to oral lavage and inhalation) administration. It is generally preferred to administer such compounds and their salts orally.

In general for uses described and claimed herein, tenidap and its salts are most desirably administered in does for oral administration ranging from about 40 mg up to about 120 mg per day for subjects having an inflammatory arthritic condition such as rheumatoid arthritis or osteoarthritis, although variations will still necessarily occur depending upon the weight of the subject being treated and/or the duration of the treatment. Further, for parenteral administration, tenidap and its salts are most desirably administered in doses from about 1 mg up to about 200 mg per day, although variations will still necessarily occur here, too, depending upon the weight of the subject being treated and/or the duration of the treatment. The appropriate dose for reducing the level of total serum cholesterol and/or reducing the level of serum LDL cholesterol and/or reducing the level of serum triglycerides in a mammal with tenidap and its salts will be readily determine by those skilled in the art of prescribing and/or administering such compounds. A preferred oral does for reducing the level of total serum cholesterol and/or reducing the level of serum LDL cholesterol in subjects suffering from rheumatoid arthritis or osteoarthritis is about 80 mg per day for oral administration. Further, data obtained for oral doses of 80 mg per day to subjects suffering from rheumatoid arthritis or osteoarthritis showed no reduction the level of serum triglycerides. This is believed to be due to other factors such as the proximity of the subjects meals o the time of sampling, particularly since oral doses or 40 mg per day and 120 mg per day result in reduction o the level of serum triglycerides. A preferred oral dose for reducing the level of serum triglycerides in subjects suffering from rheumatoid arthritis or osteoarthritis is about 120 mg per day. Nevertheless, it is still to be appreciated that other variations may also occur in this respect, depending upon the species of mammal being treated and its individual response to said medicament, as well as on the particular type of pharmaceutical formulation chosen and the time period and interval at which such administration is carried out. In some instances, dosage levels below the lower limit of the aforesaid range may be more than adequate, while in other cases still larger doses may be employed without causing any harmful or deleterious side effects to occur, provided that such higher dose levels are first divided into several smaller doses that are to be administered throughout the day.

For purposes of oral administration, tablets containing excipients such as sodium citrate, calcium carbonate and dicalcium phosphate may be employed along with various disintegrates such as starch and preferably potato or tapioca starch, alginic acid and certain complex silicates, together with binding agents such as polyvinylpyrrolidone, sucrose, gelatin and acacia. Additionally, lubricating agents such as, but not limited to, magnesium stearate, sodium lauryl sulfate and talc are often very useful for tableting purposes. Solid compositions of a similar type may also be employed as fillers in soft elastic and hard-filled gelatin capsules; preferred materials in this connection also include, by way of example and not of limitation, lactose or milk sugar as well as high molecular weight polyethylene glycols. When aqueous suspensions and/or elixirs are desired for oral administration, the essential active ingredient may be combined with various sweetening or flavoring agents, coloring matter or dyes and, if so desired, emulsifying and/or suspending agents, together with diluents such as water, ethanol, propylene glycol, glycerin and various like combinations thereof.

Although the generally preferred mode of administration of tenidap or its pharmaceutically-acceptable base salts is oral, they may be administered parentaerally as well.

For purposes of parenteral administration, solutions of tenidap or a salt thereof in sesame or peanut oil or in aqueous propylene glycol may be employed, as well as sterile aqueous solutions of the corresponding water soluble base salts previously enumerated. Such aqueous solutions should be suitably buffered if necessary and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter such as a sintered glass filter or a diatomaceous-earth or unglased porcelain filter. Preferred filters of this the include the Berkefeld, the Chamberland and the Asbestos Disk-Metal Seitz filter, wherein the fluid is sucked into the sterile container with the aid of a suction pump. The necessary steps should be taken throughout the preparation of these injectable solutions to insure that the final products are obtained in a sterile condition, for purposes of transdermal administration, the dosage form of the particular compound may include, by way of example, solutions, lotions, ointments, creams, gels, suppositories, rate-limiting sustained release formulations and devices therefor. Such dosage forms comprise the particular compound and may include ethanol, water, penetration enhancer and inert carriers such as gel-producing materials, mineral oil, emulsifying agents, benzyl alcohol and the like.

Specific transdermal flux enhancing compositions are disclosed in European Patent Application 271,983 and European Patent Application 331,382, which have been filed in the name of the assignee of this invention, the teachings of which are incorporated herein by reference. For purposes of topical administration, the dosage form of the particular compound may include, by way of example and not of limitation, solutions, lotions, ointments, creams and gels.

We claim:

1. A method of lowering total serum cholesterol in a mammal in need thereof and having an inflammatory arthritic condition which comprises administering to said mammal a total serum cholesterol lowering amount of tenidap or a pharmaceutically-acceptable base salt thereof.

2. The method according to claim 1 wherein the inflammatory arthritic condition is rheumatoid arthritis or osteoarthritis.

3. The method according o claim 2 wherein the sodium slat of tenidap is administered.

4. The method according to claim 2 wherein tenidap, or a pharmaceutically-acceptable base salt thereof, is administered orally.

5. The method according to claim 3 wherein the sodium salt of tenidap is administered orally.

6. The method according to claim 2 wherein tenidap, or a pharmaceutically-acceptable base salt thereof, is administered parentaerally.

7. The method according to claim 3 wherein the sodium salt of tenidap is administered parentaerally.

8. A method of lowering serum LDL cholesterol in a mammal in need thereof and having an inflammatory arthritic condition which comprises administering to said mammal a serum LDL cholesterol lowering amount of tenidap or a pharmaceutically-acceptable base salt thereof.

9. The method according to claim 8 wherein he inflammatory arthritic condition is rheumatoid arthritis or osteoarthritis.

10. The method according to claim 9 wherein the sodium salt of tenidap is administered.

11. The method according to claim 9 wherein tenidap, or a pharmaceutically-acceptable base salt thereof, is administered orally.

12. The method according to claim 10 wherein the sodium salt of tenidap is administered orally.

13. The method according to claim 9 wherein tenidap, or a pharmaceutically-acceptable base salt thereof, is administered parentally.

14. The method according to claim 10 wherein the sodium salt of tenidap is administered parentaerally.

15. A method of lowering serum triglycerides in a mammal in need thereof and having an inflammatory arthritic condition which comprises administering to said mammal a serum triglyceride lowering amount of tenidap or a pharmaceutically-acceptable base salt thereof.

16. The method according to claim 15 wherein the inflammatory arthritic condition is rheumatoid arthritis of osteoarthritis.

17. The method according to claim 16 wherein the sodium salt of tenidap is administered.

18. The method according to claim 16 wherein tenidap, or a pharmaceutically-acceptable base salt thereof, is administered orally.

19. The method according to claim 17 wherein eh sodium salt of tenidap is administered orally.

20. The method according to claim 16 wherein tenidap, or a pharmaceutically-acceptable base salt thereof, is administered parentally.

21. The method according to claim 17 wherein the sodium salt of tenidap is administered parentally.

* * * * *

UNITED STATES PATENT AND TRADEMARK OFFICE
CERTIFICATE OF CORRECTION

PATENT NO. : 5,122,534

DATED : June 16, 1992

INVENTOR(S) : Leland D. Loose, et al

It is certified that error appears in the above-identified patent and that said Letters Patent is hereby corrected as shown below:

At column 3, line 63, "N-methylglucamines" should read -- N-methylglucamine--;
At column 3, line 64, "pyrrolidien" should read --pyrrolidine--;
At column 3, line 66, "N-etylpiperdien" should read --N-ethylpiperdine--;
At column 4, line 29, "does" should read --doses --.
At column 4, line 46, "does" shold read --dose--;
At column 4, line 55, "meals o the" should read --meals to the--;
At column 4, line 56, "or 40 mg" should read --of 40 mg--;
At column 4, line 57, "reduction o the" should read --reduction of the--;
At column 5, line 9, "disintegrates" should read --disintegrants--;
At column 5, lines 29-30, "parentaerally" should read --parenterally--;
At column 5, line 47, "the" should read --type--;

UNITED STATES PATENT AND TRADEMARK OFFICE
CERTIFICATE OF CORRECTION

PATENT NO.   :   5,122,534
DATED        :   June 16, 1992
INVENTOR(S)  :   Leland D. Loose, et al It is certified that error appears in the above-identified patent and that said Letters Patent is hereby corrected as shown below:

At column 6, line 14, "o" should read --to--;
At column 6, line 23 "parentaerally" should read --parenterally--;
At column 6, line 25, "parentaerally" should read --parenterally--;
At column 6, line 32, "he" should read --the--;
At column 6, line 44, "parentally" should read --parenterally--;
At column 6, line 46, "parentaerally" should read --parenterally--;
At column 6, line 55, "of" should read --or--;
At column 6, line 61, "eh" should read --the--;
At column 6, line 65, "parentally" should read --parenterally--;and
At column 6, line 67, "parentally" should read --parenterally--.

Signed and Sealed this

Twenty-fourth Day of May, 1994

Attest:

BRUCE LEHMAN

Attesting Officer

Commissioner of Patents and Trademarks